United States Patent
Bailly et al.

(10) Patent No.: US 8,808,315 B2
(45) Date of Patent: Aug. 19, 2014

(54) SURGICAL INSTRUMENT FOR DEPLOYING A PROSTHESIS

(75) Inventors: Pierre Bailly, Trevoux (FR); Geneviève Doucet, Villefranche sur Saone (FR)

(73) Assignee: Sofradim Production (FR)

( * ) Notice: Subject to any disclaimer, the term of this patent is extended or adjusted under 35 U.S.C. 154(b) by 469 days.

(21) Appl. No.: 13/119,581

(22) PCT Filed: Sep. 17, 2009

(86) PCT No.: PCT/FR2009/051749
§ 371 (c)(1),
(2), (4) Date: May 27, 2011

(87) PCT Pub. No.: WO2010/031967
PCT Pub. Date: Mar. 25, 2010

(65) Prior Publication Data
US 2011/0224704 A1   Sep. 15, 2011

Related U.S. Application Data

(60) Provisional application No. 61/097,986, filed on Sep. 18, 2008.

(51) Int. Cl.
*A61B 17/08* (2006.01)
*A61B 17/10* (2006.01)

(52) U.S. Cl.
USPC .......................................... 606/151; 606/142

(58) Field of Classification Search
USPC ................................................. 606/151, 142
See application file for complete search history.

(56) References Cited

U.S. PATENT DOCUMENTS

| 3,810,467 | A | | 5/1974 | Frankenthal | |
|---|---|---|---|---|---|
| 5,258,000 | A | * | 11/1993 | Gianturco | 606/151 |
| 5,397,331 | A | * | 3/1995 | Himpens et al. | 606/151 |
| 2004/0087980 | A1 | * | 5/2004 | Ford et al. | 606/151 |

FOREIGN PATENT DOCUMENTS

| EP | 1 336 391 | 8/2003 |
|---|---|---|
| FR | 2 208 299 | 6/1974 |

OTHER PUBLICATIONS

International Search Report PCT/FR2009/051749 dated Jan. 15, 2010.

* cited by examiner

*Primary Examiner* — Gregory Anderson
*Assistant Examiner* — Christina Lauer

(57) ABSTRACT

The present invention relates to a surgical instrument (1) for deploying a prosthesis (200) and includes a first layer and second layer assembled together so as to define an internal space accessible to said surgical instrument (1) by means of an opening provided in said first layer, said surgical instrument including at least one sheet (2) made of a flexible resilient material, said sheet continuously overlapping itself one or more times so as to define a plurality of levels forming a spiral (3). The invention also relates to a kit including such a surgical instrument and such a prosthesis.

11 Claims, 4 Drawing Sheets

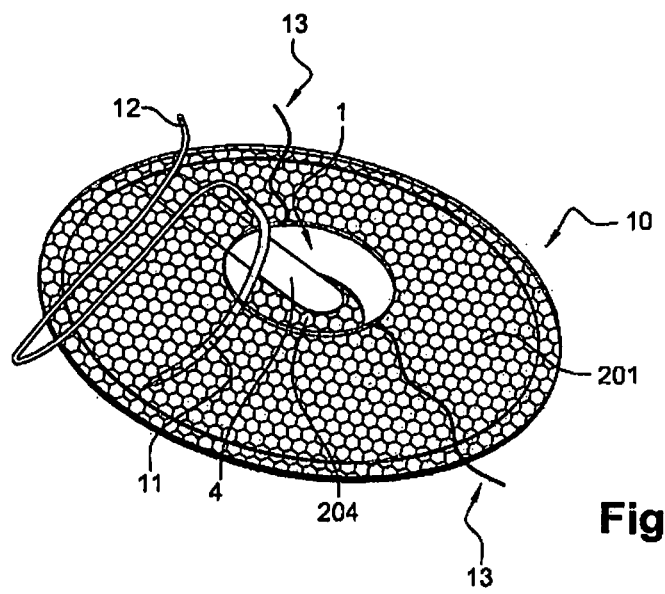
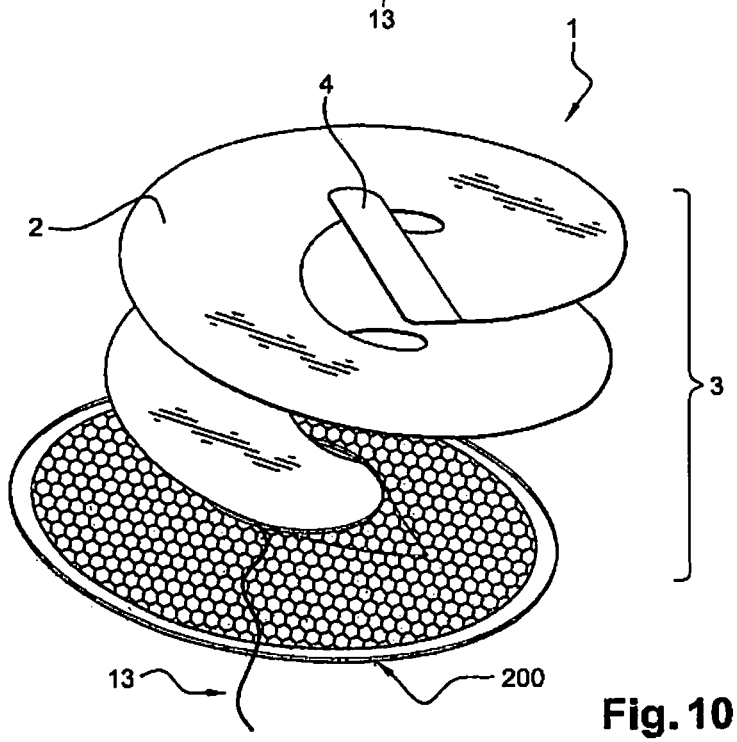

SURGICAL INSTRUMENT FOR DEPLOYING A PROSTHESIS

CROSS-REFERENCE TO RELATED APPLICATIONS

This application is a U.S. National Stage Application filed under 35 U.S.C. §371(a) of International Application No. PCT/FR2009/051749 filed Sep. 17, 2009, which claims the benefit of and priority to U.S. Provisional Application Ser. No. 61/097,986 filed Sep. 18, 2008.

The present invention relates to a surgical instrument making it possible to place a prosthesis, in particular for covering hernias, as well as a kit comprising this surgical instrument and this prosthesis.

The abdominal wall in humans is made up of fats and muscles connected to each other by fascias. A break in continuity can occur at the fascias, allowing part of the peritoneum to pass, which then constitutes a sac, or a hernia, containing either fat or part of the intestines. Hernias or incisional hernias (hernia occurring on a surgical parietal scar) manifest themselves by a protuberance on the surface of the skin and are qualified as umbilical or inguinal hernias or incisional hernias, for example, depending on where they are located.

The most traditional method for repairing a hernia involves placing stressed suture threads. However, this type of repair causes pain for the patient and, due to the significant stresses, involves a non-negligible risk of tearing of muscles and fascia by the sutures and/or a recurrence of the hernia.

In order to minimize the risks of recurrence, surgeons frequently use the placement of a synthetic lattice prosthesis that replaces or strengthens the weakened anatomical tissues without requiring that the edges of the damaged tissues be brought together. However, such a prosthesis is subject to an abdominal pressure that tends to expel it towards the outside. Yet the effectiveness of the prosthesis, and therefore the minimization of the risks of recurrence, depend in large part on the fixing thereof. First, the spreading out of the prostheses, which are often flexible, is difficult, such that they tend to form folds on the abdominal wall. The absence of complete spreading out causes a risk of engagement of the peritoneal sac and increases the chances of recurrence. It is therefore crucial for the surgeon to ensure that no part of the prosthesis is folded and that no viscus or any part of the intestines is inserted between the prosthesis and the abdominal wall. Then, poor positioning of the sutures or poor fixing of the prosthesis risks distorting the latter and creating stresses.

The present invention aims to propose a surgical instrument making it possible to facilitate the spreading out and fixing of a prosthesis that can be used for the surgical treatment of hernias and making it possible to resolve the aforementioned drawbacks, in particular, but not exclusively, for the surgical treatment of small hernias.

The present invention also relates to a surgical kit for the treatment of a hernia of the abdominal wall.

In the present application, "prosthesis" refers to a biocompatible medical device that can be implanted in the human or animal body.

A first aspect of the invention relates to a surgical instrument for deploying a prosthesis intended to fill in a hernial defect of the abdominal wall, said prosthesis including at least one first layer made from a biocompatible flexible material intended to be placed opposite the abdominal wall, and at least one second layer made from a biocompatible flexible material intended to be placed opposite the abdominal cavity, said first and second layers being assembled together so as to define an internal space accessible to said surgical instrument by means of an opening provided in said first layer, said surgical instrument including at least one sheet made of a flexible resilient material, said sheet continuously overlapping itself one or more times so as to define a plurality of levels (or layers) forming a spiral.

Due to the resilience of said sheet, the spiral is able to adopt a substantially flat configuration, in which each level is in contact with the adjacent level, corresponding to an idle configuration in which the spiral does not undergo significant stresses, or on the contrary a deployed configuration, in which no level is in contact with another level, corresponding to a configuration in which a force tending to space the two ends of the spiral away from each other is exerted. In this application, we will also refer to the surgical instrument according to the invention using the terms protective disc, or disc, or spiral.

Owing to the resilience of the material making up said sheet, the disc or spiral has a spring effect: thus if, in its flat configuration, it is folded by pressing it on itself while exerting pressure on its edges, it tends to return naturally to its flat configuration when the exerted pressure is released.

As will appear in the following description, the surgical instrument according to the invention is intended to be introduced into the prosthesis within the internal space thereof, in order to facilitate the introduction, placement and deployment of the prosthesis in the implantation site. The surgical instrument must then be removed from the prosthesis once the latter is fixed to the implantation site.

In one embodiment of the invention, the upper end of the spiral (or disc) comprises a removal tab. Thus, once the prosthesis is correctly deployed and positioned, then fixed, the surgeon can remove the surgical instrument or disc from the prosthesis by pulling on the removal tab: he then deploys the disc, which extends in the form of a spiral, and the surgeon can then easily remove the disc by causing it to rotate around itself, or more easily by exerting a simple upward linear traction on the tab: given its shape and material, preferably having a low friction coefficient relative to the prosthesis, the spiral unwinds automatically.

In one embodiment of the invention, the material making up said sheet is a polymer chosen from polypropylene, polyethylene, polytetrafluoroethylene (PTFE), and/or mixtures thereof, for example having a low friction coefficient with the prosthesis to facilitate the removal thereof.

The present invention also relates to a surgical kit for treating a hernia of the abdominal wall comprising:

a surgical instrument as described above;

and a prosthesis intended to fill in said defect, said prosthesis comprising at least one layer of a biocompatible flexible material intended to be placed opposite the abdominal wall and at least one second biocompatible flexible material intended to be placed opposite the abdominal cavity, said first and second layers being assembled to each other so as to define an open inner space using an opening formed in said first layer.

In one embodiment, the surgical kit according to the invention includes a plurality of centering threads intended to be connected to said prosthesis around the perimeter of said opening. It is understood that the centering threads can be fixed to the prosthesis beforehand or that said centering threads could be fixed later by the surgeon and/or removed at the end of the operation.

In one embodiment of the surgical kit, at least one of the layers of said prosthesis is made up of an arrangement of threads. Preferably, both layers are made up of an arrangement of threads.

In one embodiment of the invention, the second layer of said prosthesis of the kit is covered with an anti-adhesive coating on its face intended to be placed opposite the abdominal cavity.

Within the meaning of this application, "anti-adhesive" refers to a smooth and non-porous biocompatible material or coating not offering any room for cellular recolonization.

The anti-adhesive coating according to the present invention makes it possible to protect, at least during the initial scarring phase, the second layer of said prosthesis, i.e. it is not exposed to inflammatory cells, such as granulocytes, monocytes, macrophages, or multinuclear giant cells generally activated by the surgery. Indeed, at least during the initial scarring phase, the length of which can vary from about 5 to 10 days, only the anti-adhesive coating is accessible by the different factors such as proteins, enzymes, cytokines, or inflammatory line cells, at the first textile portion.

In the event the anti-adhesive coating is made up of non-resorbable materials, it thus protects the coated prosthesis layer before and after implantation, throughout the entire implantation time of the prosthesis.

Moreover, owing to the anti-adhesive coating, the fragile surrounding tissues such as the hollow viscera, for example, are protected, in particular from the formation of unwanted severe post-surgical fibrous adhesions.

In the event the anti-adhesive material comprises a bioresorbable material, it is preferable to choose a bioresorbable material that does not resorb until several days have passed so that the anti-adhesive coating can perform its function of protecting the intestine and the hollow organs during the days following the operation, and, until the cellular rehabilitation of the prosthesis in turn protects the fragile organs.

Other features and advantages of the invention will appear upon reading the following description of one particular embodiment, provided solely as a non-limiting example, in which the prosthesis is a reinforcement of the abdominal wall.

FIG. 9 is a perspective view of the kit of FIG. 7, once redeployed in the implantation site (the latter not being shown);

FIG. 10 is a perspective view of the step for removing the surgical instrument from the prosthesis, once the latter is fixed in the implantation site (the latter not being shown).

Figure 1:
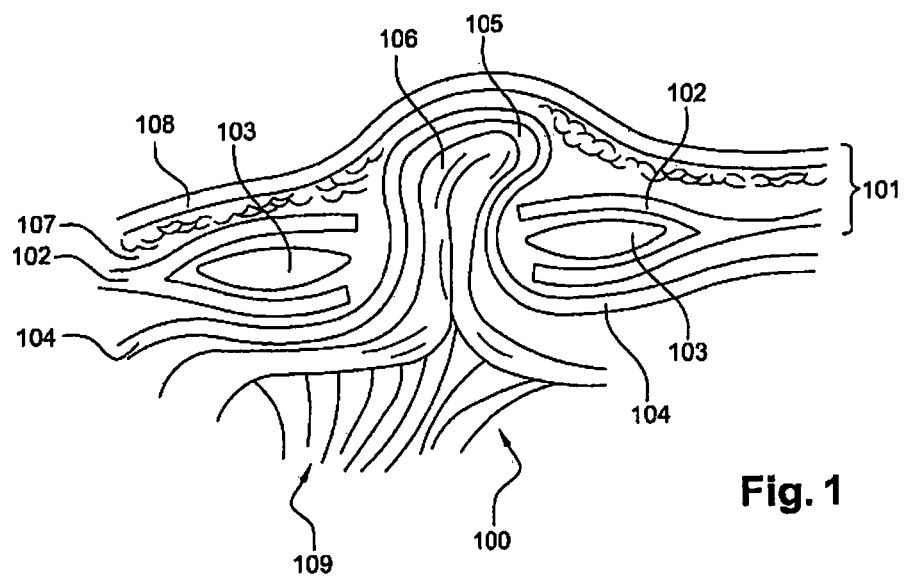
FIG. 1 is a cross-sectional view of an abdominal median hernia or incisional hernia.

FIG. 1 shows a hernia 100 of the abdominal wall 101 that is characterized by a break in the continuity of the fascia 102 surrounding the rectus muscles 103 and a passage of the peritoneum 104 forming a sac, the hernial sac 105, which contains either fat (omentum) or part of the viscera 106, and then exerts pressure on the fatty tissues 107 and is flush with the skin 108. Hernia treatment 100 consists of replacing and maintaining the viscera 106 in the abdominal cavity 109.

Figure 2:
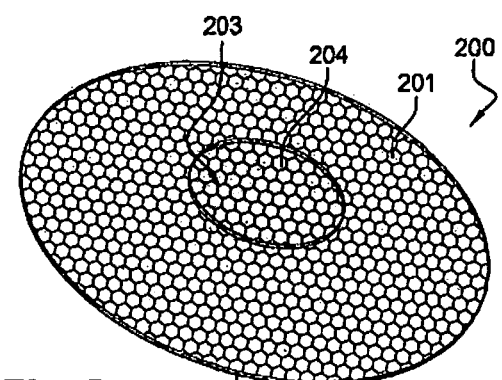
FIG. 2 is a perspective view of a prosthesis contained in the kit according to the present invention.
Figure 3:
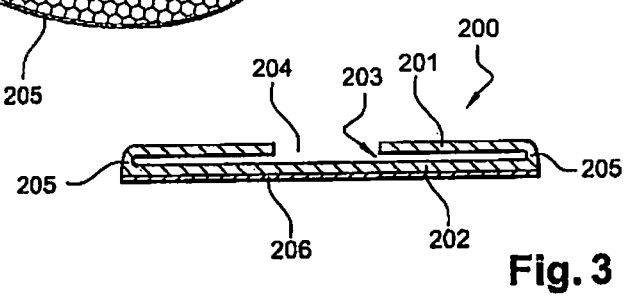
FIG. 3 is a cross-sectional illustration of the prosthesis of FIG. 2.

FIGS. 2 and 3 show a prosthesis 200 able to fill in a hernial defect 100 like that shown in FIG. 1, said prosthesis 200 comprising at least one first layer 201 of biocompatible flexible material intended to be placed opposite the abdominal wall 101 and at least one second layer 202 of biocompatible material intended to be placed opposite the abdominal cavity 109. Said first and second layers (201, 202) are assembled to each other so as to define an inner space 203 open via an opening 204 formed in said first layer 201 and extending to the assembly zone of said first and second layers 201, 202.

In the illustrated example, the first layer 201 and the second layer 202 are made up of arrangements of threads, such as tissues, non-wovens or knits, and they are assembled on their periphery by a seam 205. The threads forming the layers (201, 202) can be chosen among resorbable and/or non-resorbable threads 206. In the illustrated example, an anti-adhesive coating 206, which is preferably bioresorbable, advantageously covers the outer surface of the second layer 202 in order to avoid in particular the formation of unwanted severe post-surgical fibrous adhesions.

Figure 4:
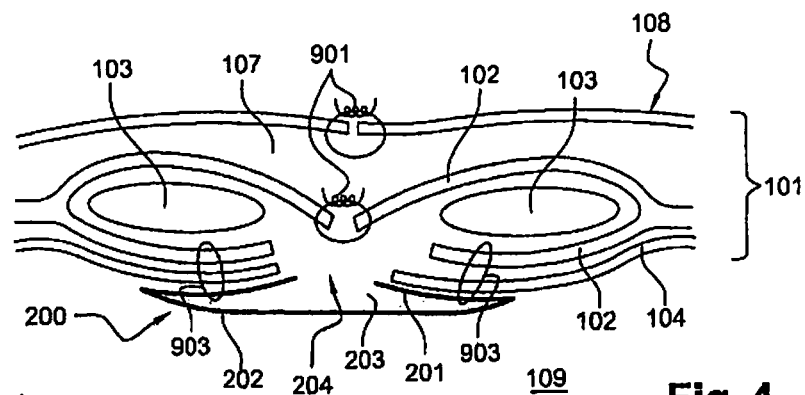
FIG. 4 is a cross-sectional diagrammatic illustration of the abdominal wall showing a repair of a hernia that has been done using a surgical kit according to the present invention.

The prosthesis 200 of FIGS. 2 and 3 is intended to repair a hernia 100 like that of FIG. 1, and must be positioned, after implantation, as shown in FIG. 4. In that figure, the prosthesis 200 is diagrammed, after reduction of the hernial sac 105, as placed to fill in the hernial defect 100: as shown in this figure, in which sutures (901; 903) are diagrammed, the surgeon has made an incision in the skin 108 and the fascia 102 to introduce the prosthesis 200 into the hernial defect; he has then arranged the prosthesis 200, with its first layer 201 opposite the abdominal wall 101 and its second layer 202 opposite the abdominal cavity 109; he has fixed the prosthesis 200 by suturing the layer 201 to the fascia 102 and the peritoneum 104 using sutures 903, then he has closed the initial incisions of the fascia 102 and the skin 108 using sutures 901.

During such an operation, the difficulty lies in the introduction and deployment of the prosthesis 200, in particular its spreading out and placement against the abdominal wall 101, whereas moreover the initial incisions in the skin 108 and the fascia 102 needing to be as small as possible, the surgeon's workspace and visibility are particularly limited.

Figure 5:
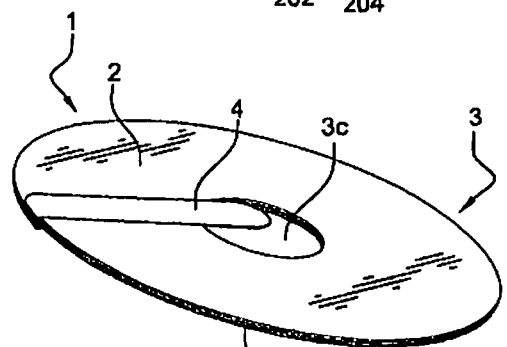
FIG. 5 is a perspective view of an embodiment of the surgical instrument according to the invention, in its flat configuration.
Figure 6:
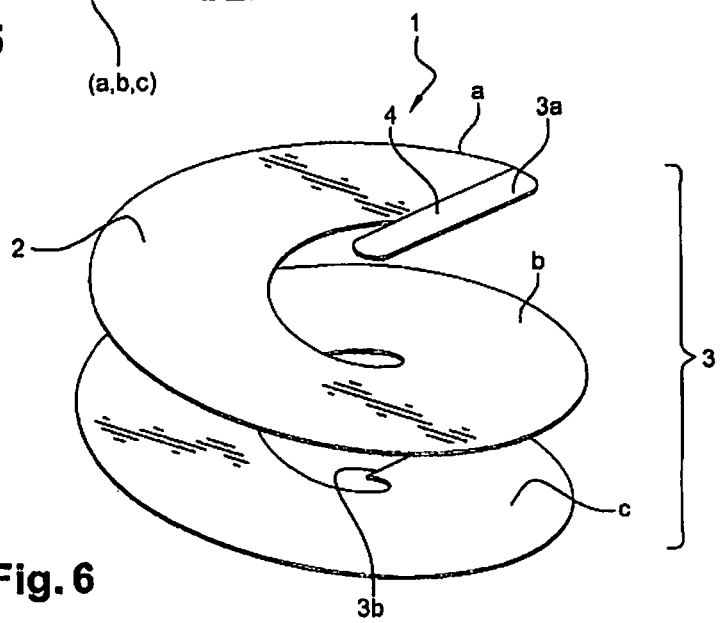
FIG. 6 is a perspective view of the surgical instrument of FIG. 5, in its deployed configuration.

FIGS. 5 and 6 show an embodiment of a surgical instrument 1 according to the invention, said instrument 1 being particularly useful for the introduction and deployment of the prosthesis 200 during the operation described above.

As shown in FIGS. 5 and 6, the surgical instrument 1 according to the invention comprises at least one sheet 2 made from a flexible and resilient material, said sheet 2 overlapping itself one or several times, continuously, so as to define several layers or levels (a, b, c) forming a spiral 3. As shown in FIG. 6, the spiral 3 is finite (or limited) and has two opposite ends, an upper end 3a and a lower end 3b. Due to the resilience of said sheet 2, the spiral 3 can adopt a substantially flat configuration, in which each level (a, b, c) is in contact with the adjacent level (a, b, c), corresponding to an idle configuration in which the spiral 3 does not undergo significant stresses: this configuration is shown in FIG. 5. Alternatively, the spiral 3 can adopt a deployed configuration, in which no level (a, b, c) is in contact with another level, corresponding to a configuration in which a force, for example exerted by the surgeon, tending to move the two ends (3a, 3b) of the spiral 3 away from each other is exerted: this configuration is shown in FIG. 6. The surgical instrument is thus capable of adopting two configurations: a flat configuration, as shown in FIG. 5, and a deployed configuration, as shown in FIG. 6.

As appears in FIG. 5, in its flat configuration, the spiral 3, due to the small thickness of the sheet 2, forms a flat disc, provided with a central hole 3c.

The material making up said sheet 2 is preferably a polymer of the polypropylene, polyethylene, or polytetrafluoroethylene (PTFE) type; such a polymer makes it possible to give the sheet the necessary resilience to go from its flat spiral configuration to its deployed spiral configuration. Moreover, as will appear from the continuation of the description, the material making up said sheet 2 allows the surgical instrument 1, when it is in its flat spiral configuration shown in FIG. 5, to be folded in half on itself under the effect of a pressure exerted on two opposite edges, for example according to a fold corresponding to one of its diameters: in such a case, due to the resilience of the sheet 2, the surgical instrument 1 tends to return naturally to its flat configuration when the exerted pressure is released.

The disc or surgical instrument 1 thus has properties of resilience (redeployment after folding), rigidity (maintenance of the prosthesis against the abdominal wall), flexibility (facilitating removal thereof): the surgical instrument 1 according to the invention also plays a protective role, as will appear later, in the area of the seam 205 of the prosthesis, during fixing of the latter to the abdominal wall, against any perforations by the suture needles or the stapler insertions.

As appears in FIG. 6, the upper end 3a of the spiral (or disc) 3 comprises a removal tab 4.

The surgical instrument 1 can be introduced extremely easily into a prosthesis 200 as shown in FIG. 2: indeed, to do so, one need only, by using the spiral 3 of the sheet 2 in its deployed form as shown in FIG. 6, introduce the lower end 3b of the spiral 3 into the opening 204 of the prosthesis, then rotate the spiral 3 relative to the prosthesis 200 by making the sheet 2 slide in the inner space 203 of the prosthesis 200.

Preferably, the material making up the sheet 2 has a low friction coefficient relative to the prosthesis 200 to facilitate both its introduction into the prosthesis 200, and as will be seen later, its removal. For example, if the threads making up the prosthesis are made from polyester, or polypropylene, and the sheet 2 is made from polypropylene, or polytetrafluoroethylene, the sheet 2 will slide easily against the prosthesis 200 because polyester and polypropylene have a low friction coefficient relative to polypropylene and polytetrafluoroethylene.

Figure 7:
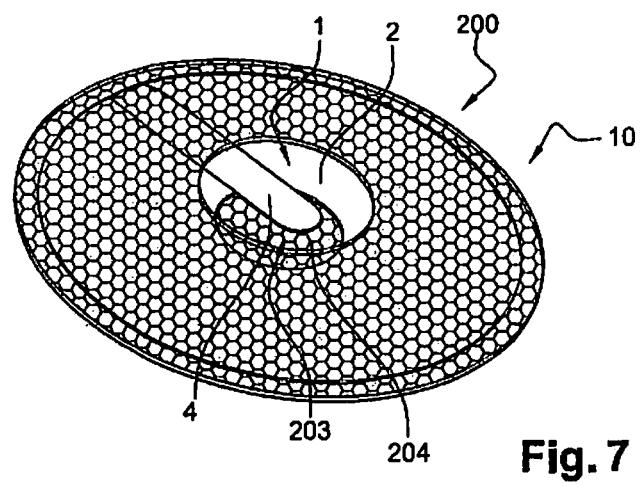
FIG. 7 is a perspective view of one embodiment of the kit according to the invention, the surgical instrument being completely introduced into the inner space of the prosthesis.

In this way, the sheet 2 can be introduced completely into the inner space 203 of the prosthesis 200, as shown in FIG. 7. As appears in that figure, once the surgical instrument 1 is completely introduced into the prosthesis 200, the spiral 3 is replaced in its flat configuration (corresponding to FIG. 5), with the removal tab 4, situated at the upper end 3a of the spiral 3, visible through the opening 204.

Figure 8:
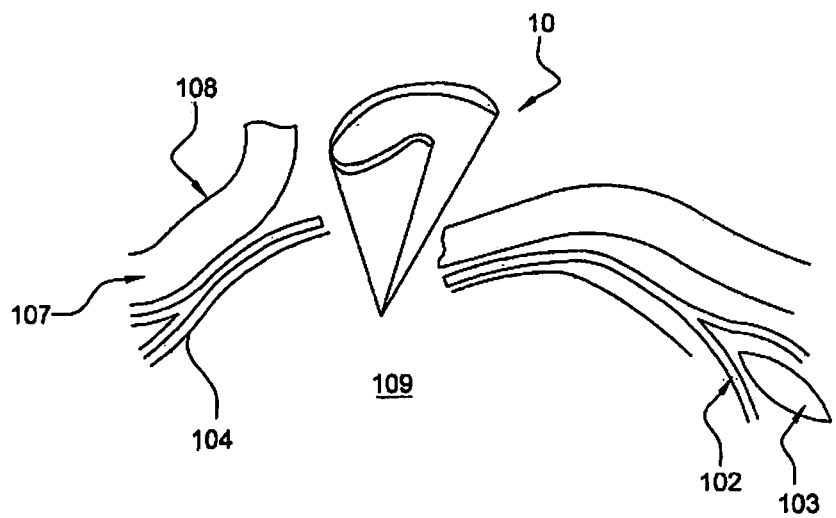
FIG. 8 is a diagrammatic cross-sectional illustration of the abdominal wall showing the introduction into the implantation site of the kit of FIG. 7.

The kit 10 thus made up of the prosthesis 200 and the surgical instrument 1 completely introduced into the open space 203 of the prosthesis 200, is completely flat. Due to the resilience of the sheet 2 forming the surgical instrument 1 and the natural flexibility of the prosthesis 200, the layers (201, 202) of which are arrangements of threads, the surgeon can grasp the kit 100 (prosthesis 200+instrument 1) and fold it in two, or even in four, as shown in FIG. 8, by exerting pressure on the edges of the kit 10 in order to introduce it into the implantation site in the abdominal cavity 109 through the incisions formed at the skin 108 and the fascia 102. Because it is folded on itself, the kit 10 takes up little space and is easily introduced into small incisions.

Once in the abdominal cavity 109, the kit 10 redeploys naturally, owing to the resilience of the sheet 2, which tends to return naturally to its flat spiral position 3 (corresponding to FIG. 5). FIG. 9 shows the kit 10, as redeployed in the abdominal cavity: in this figure, however, for clarity reasons, the implantation site has not been shown again. Owing to the presence of the surgical instrument 1, its shape and its structure, and in particular its resilient properties, the surgeon then knows that the prosthesis 200 is completely deployed, and that its layer 201 in particular is advantageously pressed against the fascia 102 of the abdominal wall, without forming folds that risk causing unfortunate sutures with fragile surrounding organs such as the viscera. The surgeon can then suture the layer 201 of the prosthesis 200 to the fascia 102 of the abdominal wall, using a needle 11 and thread 12 for example, as shown in FIG. 9. He thus performs the sutures 903 shown in FIG. 4, on the periphery of the prosthesis 200, thereby forming fastening means for fastening the prosthesis 200. Alternatively, the surgeon could use a stapler, for example a laparoscopy stapler, and staples as fastening means. During this operation, the surgical instrument 1 according to the invention plays a protective role to protect the surrounding viscera, in particular in the vicinity of the seam 205 of the prosthesis 200, by avoiding, due to the presence of the sheet 2 that forms a barrier, any perforations of these viscera by the suture needles or the insertions by the stapler.

During this operation, the surgeon can be assisted, to center the kit 10, and therefore the prosthesis 200, on the defect to be filled in, by centering threads 13, already bound, or that he has bound beforehand, to the prosthesis 200 on the perimeter of the opening 204 thereof, as shown in FIG. 9. These centering threads 13 are preferably removed once the prosthesis 200 is attached.

Once the prosthesis 200 is thus attached, the surgeon can remove the surgical instrument 1, by removing the prosthesis 200 through the opening 204: to that end, he pulls on the sheet 2 using the removal tab 4, which he grasps easily through the opening 204, and he deploys the spiral 3 while making it rotate relative to the prosthesis 200, as shown in FIG. 10. The surgical instrument 1 is thus easily removed from the prosthesis 200, in particular when the friction coefficient of the material making up the sheet 2 is low relative to the prosthesis 200.

The surgeon then needs only close the initial incisions of the fascia 102 and the skin 106 using sutures 901 as shown in FIG. 4.

The surgical instrument 1 according to the invention thus allows a deployment and spreading out of the prosthesis 200 that are as effective as possible during an operation to reduce a hernial defect. In particular, due to its spring effect and its ability to stiffen the prosthesis, the surgical instrument according to the invention makes it possible both to reduce the space occupied by the prosthesis when it is introduced into the implantation site, and to perform optimal pressing of the latter against the abdominal wall, thereby making it possible to avoid the formation of unwanted folds within the prosthesis.

The present invention also pertains to a method for treating or preventing a hernia in the umbilical region, by using a prosthesis and a surgical instrument (or disc) as described above and comprising the following steps:

One has a prosthesis and a surgical instrument (or disc or spiral) as described above: in one embodiment of the invention, the disc, in its flat configuration, is already housed in the prosthesis; in another embodiment, the surgeon introduces the disc, in its flat form, inside the prosthesis: the latter is thus completely deployed and slightly stiffened by the sheet of material making up the disc;

An incision is made on the abdominal wall at the hernial defect;

After treating the hernia, said prosthesis, in which the disc is housed, is inserted into the incision by folding it by exerting pressure on the edges of the disc;

Owing to its spring effect, the disc deploys in the abdominal cavity, bringing about the spreading out of the prosthesis; said prosthesis is positioned against the abdominal wall, centering it on the defect, for example by pulling on the centering threads of the prosthesis, the sheet of material of the disc stiffening the prosthesis and pressing it against the abdominal wall such that viscera are prevented from being inserted between said prosthesis and the abdominal wall; a correct spreading out of said prosthesis is thus ensured;

The prosthesis is fixed against the abdominal wall owing to fastening means;

One then pulls on the removal tab situated at the upper end of the spiral of the disc; in so doing, one deploys the spiral and removes the disc by making it rotate slowly around itself.

The invention claimed is:

1. A surgical kit for treating a hernia of the abdominal wall comprising:
    a prosthesis comprising at least one first layer of a biocompatible flexible material intended to be placed opposite the abdominal wall and at least one second layer of biocompatible flexible material intended to be placed opposite the abdominal cavity, said first and second layers being assembled to each other so as to define an inner space accessible by an opening formed in said first layer, and,
    a surgical instrument comprising at least one sheet made of a flexible resilient material, said sheet continuously overlapping itself one or more times so as to define a plurality of levels forming a spiral, wherein the surgical instrument is introduced into the inner space of the prosthesis to facilitate the introduction, placement and deployment of the prosthesis to the site of implantation.

2. The surgical kit according to claim 1, further comprising a plurality of centering threads intended to be connected to said prosthesis around a perimeter of said opening.

3. The surgical kit according to claim 1, wherein at least one of the layers of said prosthesis is made up of an arrangement of threads.

4. The surgical kit according to claim 1, wherein both layers are made up of an arrangement of threads.

5. The surgical kit according to claim 1, wherein the second layer of said prosthesis of the kit is covered with an anti-adhesive coating on a face of the second layer intended to be placed opposite the abdominal cavity.

6. The surgical kit according to claim 1, wherein said spiral is able to adopt a substantially flat configuration, in which each level is in contact with an adjacent level, corresponding to an idle configuration in which the spiral does not undergo significant stresses, or on the contrary a deployed configuration, in which no level is in contact with another level, corresponding to a configuration in which a force tending to space the two ends of the spiral away from each other is exerted.

7. The surgical kit according to claim 1, wherein the surgical instrument is removed from the prosthesis once the prosthesis is fixed to an implantation site.

8. The surgical kit according to claim 7, wherein an upper end of the spiral comprises a removal tab.

9. The surgical kit according to claim 1, wherein the sheet is made from a polymer chosen from polypropylene, polyethylene, polytetrafluoroethylene, and mixtures thereof.

10. The surgical kit according to claim 1, wherein the sheet has a low friction coefficient relative to the prosthesis to facilitate introduction into the prosthesis.

11. The surgical kit according to claim 1, wherein the surgical instrument includes a central hole.

\* \* \* \* \*